United States Patent
Yoshihara et al.

(10) Patent No.: US 9,046,451 B2
(45) Date of Patent: Jun. 2, 2015

(54) METHOD AND APPARATUS FOR BENDING LONG MEMBER, AND METHOD FOR BENDING DOOR FRAME

(71) Applicant: SHIROKI CORPORATION, Kanagawa (JP)

(72) Inventors: Jiro Yoshihara, Kanagawa (JP); Kazuyuki Takagi, Kanagawa (JP); Akinori Matubara, Kanagawa (JP); Yuji Mori, Kanagawa (JP)

(73) Assignee: SHIROKI CORPORATION, Kanagawa (JP)

( * ) Notice: Subject to any disclaimer, the term of this patent is extended or adjusted under 35 U.S.C. 154(b) by 31 days.

(21) Appl. No.: 13/794,856

(22) Filed: Mar. 12, 2013

(65) Prior Publication Data
US 2013/0205912 A1 Aug. 15, 2013

Related U.S. Application Data

(63) Continuation of application No. PCT/JP2011/070927, filed on Sep. 14, 2011.

(30) Foreign Application Priority Data

Oct. 13, 2010 (JP) ................. 2010-230502

(51) Int. Cl.
*G01N 3/00* (2006.01)
*G01N 3/08* (2006.01)
(Continued)

(52) U.S. Cl.
CPC .. *G01N 3/08* (2013.01); *B21D 7/00* (2013.01); *B21D 7/14* (2013.01)

(58) Field of Classification Search
CPC .................................. B21D 7/025; B21D 7/14

USPC ........................................................ 73/794
See application file for complete search history.

(56) References Cited

U.S. PATENT DOCUMENTS 7,021,155 B2* 4/2006 Imamura ........................ 73/797

FOREIGN PATENT DOCUMENTS

| JP | 53-120669 A | 10/1978 |
|----|----|----|
| JP | 11-290962 A | 10/1999 |
| JP | 2000-237825 A | 9/2000 |
| JP | 2001-150045 A | 6/2001 |

OTHER PUBLICATIONS

Machine translation of JP11290962A, Date Oct. 26, 1999, Publisher: Japanese Patent Office and National Center for Industrial Property, pp. 11.*

(Continued)

*Primary Examiner* — Harshad R Patel
(74) *Attorney, Agent, or Firm* — Millen, White, Zelano & Branigan, P.C.

(57) ABSTRACT

A method of bending a long member includes applying a tensile force to the long member to draw out the long member in a lengthwise direction thereof, measuring a displacement of the long member after commencement of the application of the initial tensile force, and bending the long member by applying a correction tensile force and a bending pressure for bending the long member into a curved shape in the lengthwise direction simultaneously to the long member upon the displacement exceeding a predetermined tensile fracture threshold value within a predetermined period of time or after a lapse of the predetermined period of time without the displacement exceeding the tensile fracture threshold value. The correction tensile force is smaller than the tensile force at the time the displacement exceeds the tensile fracture threshold value or the tensile force at the lapse of the predetermined period of time.

6 Claims, 8 Drawing Sheets

(51) Int. Cl.
*B21D 7/00* (2006.01)
*B21D 7/14* (2006.01)

(56) References Cited

OTHER PUBLICATIONS

Machine translation of JP2000237825A, Date Sep. 5, 2000, Publisher: Japanese Patent Office and National Center for Industrial Property, pp. 10.*

International Search Report for PCT/JP2011/070927 dated Nov. 8, 2011.
Shiroki "Stabilization in Precision of Bending Process of Aluminum Extrusion" Journal of Technical Disclosure No. 2005-505666 of the "Journal of Technical Disclosure of Japan Institute of Invention and Innovation" [Oct. 18, 2005] 5 pages.
English Translation Abstract of JP2001-150045 dated Jun. 5, 2001.
English Translation Abstract of JP2000-237825 dated Sep. 5, 2000.
English Translation Abstract of JP53-120669 dated Oct. 21, 1978.
English Translation Abstract of JP11-290962 dated Oct. 26, 1999.

* cited by examiner

FIG.2A

| Time Taken until Exceeding Tensile Fracture Threthhold Value D | Correction Tensil Force Value |
|---|---|
| T1 | A |
| T2 | B |
| T3 | C |

FIG.2B

| Displacement d of long Member W at a Lapse of Predetermined Period of Time | Correction Tensil Force Value |
|---|---|
| d1 | X |
| d2 | Y |
| d3 | Z |

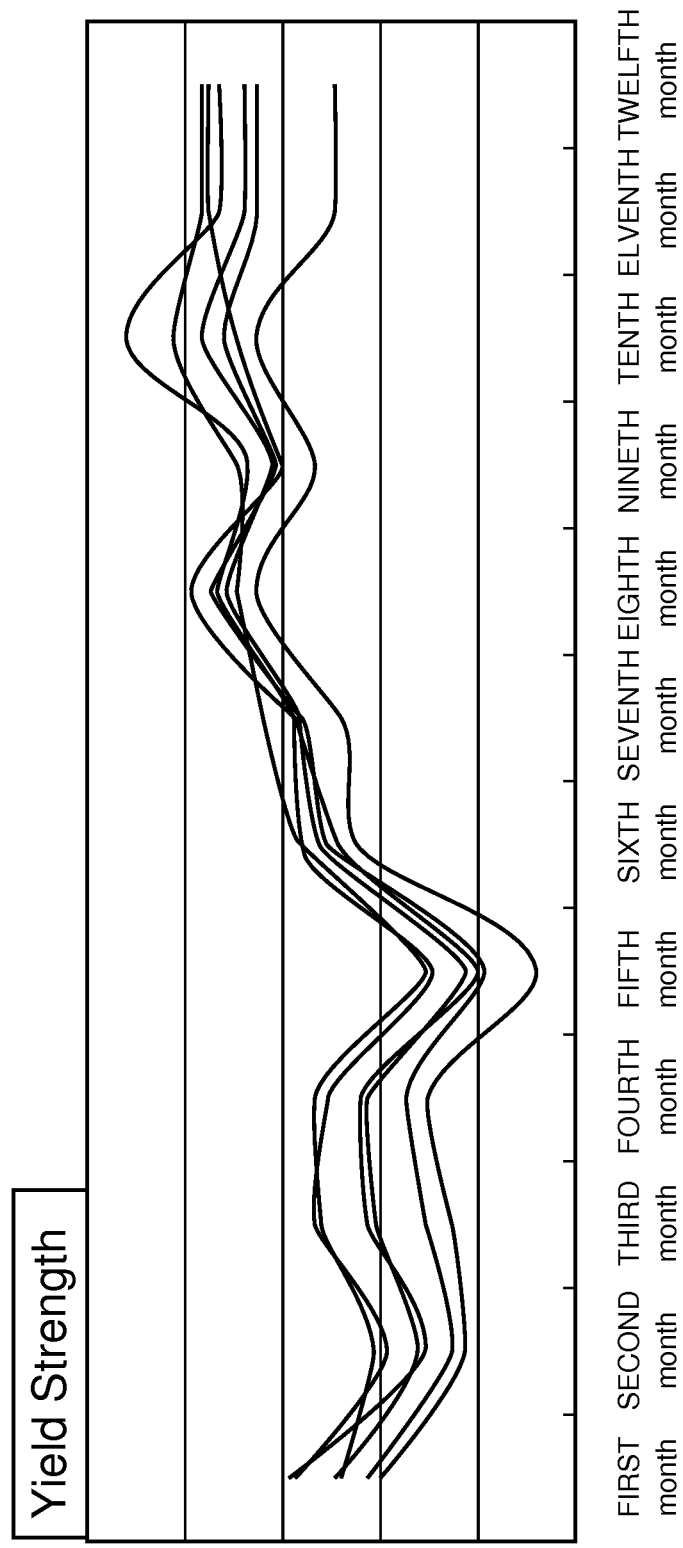

METHOD AND APPARATUS FOR BENDING LONG MEMBER, AND METHOD FOR BENDING DOOR FRAME

RELATED APPLICATION DATA

This is a continuation of International Application No. PCT/JP2011/070927, with an international filing date of Sep. 14, 2011, which is herein incorporated by reference in its entirety.

TECHNICAL FIELD

The present invention relates to a method and apparatus for bending a long member made of aluminum, iron or the like to produce, e.g., a vehicle door frame.

BACKGROUND ART

FIG. 6 is a flowchart showing a conventional process of bending a long member. First, a tensile force is applied to a long member in a single uniform manner for a predetermined period of time to draw out the long member in the lengthwise direction (S1, S2: YES), and a bending pressure is applied to the long member to bend the long member into a curved shape in the lengthwise direction thereof after the tensile force is reduced in accordance with the drawn-out amount of the long member (S3, S4, S5).

CITATION LIST

Patent Literature

Non-Patent literature 1: Journal of Technical Disclosure No. 2005-505666 in Journal of technical disclosure of Japan Institute of Invention and Innovation However, in the aforementioned prior art, since a tensile force is applied to long members in a single uniform manner for a predetermined period of time, if the long members are low in tensile strength, it is often the case that the long members cannot acceptably pass as a commodity product as a result of cross-sectional distortion, deformation or rupture (tensile fracture) caused by an excessive elastic fracture or permanent deformation occurring upon a lapse of the predetermined period of time. As shown in FIG. 7, the tensile strength of each long member is proportional to the hardness of the material thereof as a general rule; however, due to slight difference in length and sectional area caused by weight reduction and wall-thickness reduction in recent years, the value of tensile strength varies widely for different long members even if the materials thereof have the same hardness in a lot that is identical in name and in notation. In addition, even in the case of long members of the same material, long members made of aluminum, which have come to be referred to as "seasonal products", particularly vary widely in tensile strength depending on the season, temperature and humidity. FIG. 8 shows variations in tensile strength of aluminum-made products of the same lot. Accordingly, in the above described conventional art, it has been difficult to perform a favorable bending process on long members which vary widely in tensile strength, especially long members which are low in tensile strength.

The present invention has been devised based on the awareness of the above-mentioned issues, and an object of the present invention is to obtain a long-member bending method and apparatus, and a door frame bending method, each of which makes it possible to perform a favorable bending process on long members which vary widely in tensile strength, especially long members which are low in tensile strength.

SUMMARY OF THE INVENTION

The present invention has been accomplished based on the finding that, upon revising the conventional technical common knowledge of a tensile force being applied to long members (door frames) in a single uniform manner for a predetermined period of time, it is possible to perform a favorable bending process even on a long member which is low in tensile strength without causing tensile fracture if the displacement from the commencement of the application of an initial tensile pressure is measured (monitored) on each long member and if, upon the displacement of a long member exceeding a predetermined tensile fracture threshold value within a predetermined period of time or after a lapse of this predetermined period of time without the displacement of the long member exceeding this predetermined tensile fracture threshold value, a correction tensile force which is smaller than the tensile force at that time is immediately set and thereupon a bending process is performed by applying this correction tensile force and a bending pressure to the long member so that the lengthwise direction thereof becomes curved.

Namely, a long-member bending method according to the present invention is characterized by including a applying a tensile force, which increases from an initial tensile force, to the long member to draw out the long member in a lengthwise direction thereof; measuring a displacement of the long member after commencement of the application of the initial tensile force; and a bending the long member by applying a correction tensile force and a bending pressure for bending the long member into a curved shape in the lengthwise direction simultaneously to the long member upon the displacement exceeding a predetermined tensile fracture threshold value within a predetermined period of time or after a lapse of the predetermined period of time without the displacement exceeding the tensile fracture threshold value, wherein the correction tensile force is smaller than the tensile force at the time the displacement exceeds the tensile fracture threshold value or the tensile force at the lapse of the predetermined period of time.

In the present specification, "tensile fracture" refers to the phenomenon of a defect, such as cross-sectional distortion, deformation or a rupture caused by an excessive elastic fracture or permanent deformation, occurring in a long member when this long member is drawn out in the lengthwise direction for a long period of time so that this long member cannot acceptably pass as a commodity product.

In the present specification, "tensile fracture threshold value" refers to a displacement which may cause tensile fracture if a long member is further drawn out when it is drawn out in the lengthwise direction by an application of a tensile force to the long member (or a displacement slightly smaller than such a displacement). Namely, no tensile fracture has yet occurred at the moment the displacement of the long member exceeds the tensile fracture threshold value, so that tensile fracture can be reliably prevented from occurring if, immediately after the displacement of the long member exceeds the predetermined tensile fracture threshold value, the tensile force applied to the long member is changed to a correction tensile force which is smaller than the tensile force at that time.

During the bending, upon the displacement of the long member after the commencement of the application of the initial tensile force exceeding the predetermined tensile fracture threshold value within the predetermined period of time, it is desirable for a plurality of correction tensile force values to be selectively set in accordance with a time taken until the displacement exceeds the tensile fracture threshold value.

This makes it possible to set an optimum correction tensile force to perform a favorable bending process on each long member which is low in tensile strength and in which tensile fracture may occur.

During the bending, upon the predetermined period of time elapsing without the displacement of the long member, after the commencement of the application of the initial tensile force, exceeding the tensile fracture threshold value, it is desirable for a plurality of correction tensile force values are selectively set in accordance with the amount of displacement of the long member at the lapse of the predetermined period of time.

This makes it possible to set an optimum correction tensile force to perform a favorable bending process on each long member which has a degree of tensile strength such a tensile fracture cannot occur.

The present invention is characterized by an apparatus for bending a long member, including a bender which applies a variable tensile force for drawing out the long member in a lengthwise direction thereof and a bending pressure for bending the long member into a curved shape in the lengthwise direction to the long member; a displacement measurer which measures, when the variable tensile force which increases from an initial tensile force is applied to the long member by the bender, a displacement of the long member caused by the variable tensile force; and a controller which commands, when the displacement of the long member that is measured by the displacement measurer exceeds a tensile fracture threshold value within a predetermined period of time or the predetermined period of time elapses without the displacement of the long member that is measured by the displacement measurer exceeding the tensile fracture threshold value, the bender to apply the bending pressure to the long member after changing the variable tensile force of the bender to a correction tensile force which is smaller than the variable tensile force at the time the displacement exceeds the tensile fracture threshold value or a correction tensile force which is smaller than the variable tensile force at the lapse of the predetermined period of time.

The present invention is characterized by a method of bending a door frame, including applying a tensile force which increases from an initial tensile force to the door frame to draw out the door frame in a lengthwise direction thereof; measuring a displacement of the door frame after commencement of the application of the initial tensile force; and bending the door frame by applying a correction tensile force and a bending pressure for bending the door frame into a curved shape in the lengthwise direction simultaneously to the door frame upon the displacement exceeding a predetermined tensile fracture threshold value within a predetermined period of time or after a lapse of the predetermined period of time without the displacement exceeding the tensile fracture threshold value, wherein the correction tensile force is smaller than the tensile force at the time the displacement exceeds the tensile fracture threshold value or the tensile force at the lapse of the predetermined period of time.

ADVANTAGEOUS EFFECTS OF THE INVENTION

According to the prevent invention, a long-member bending method and apparatus, and a door frame bending method, each of which makes it possible to perform a favorable bending process on long members which vary widely in tensile strength, especially long members which are low in tensile strength, can be achieved.

BRIEF DESCRIPTION OF THE DRAWINGS

FIGS. 2A and 2B are charts showing examples of data stored in a correction tensile force holding table;

FIG. 8 is a diagram showing a dispersion of the tensile strength values of long members made of aluminum.

DESCRIPTION OF THE EMBODIMENT

Figure 1:
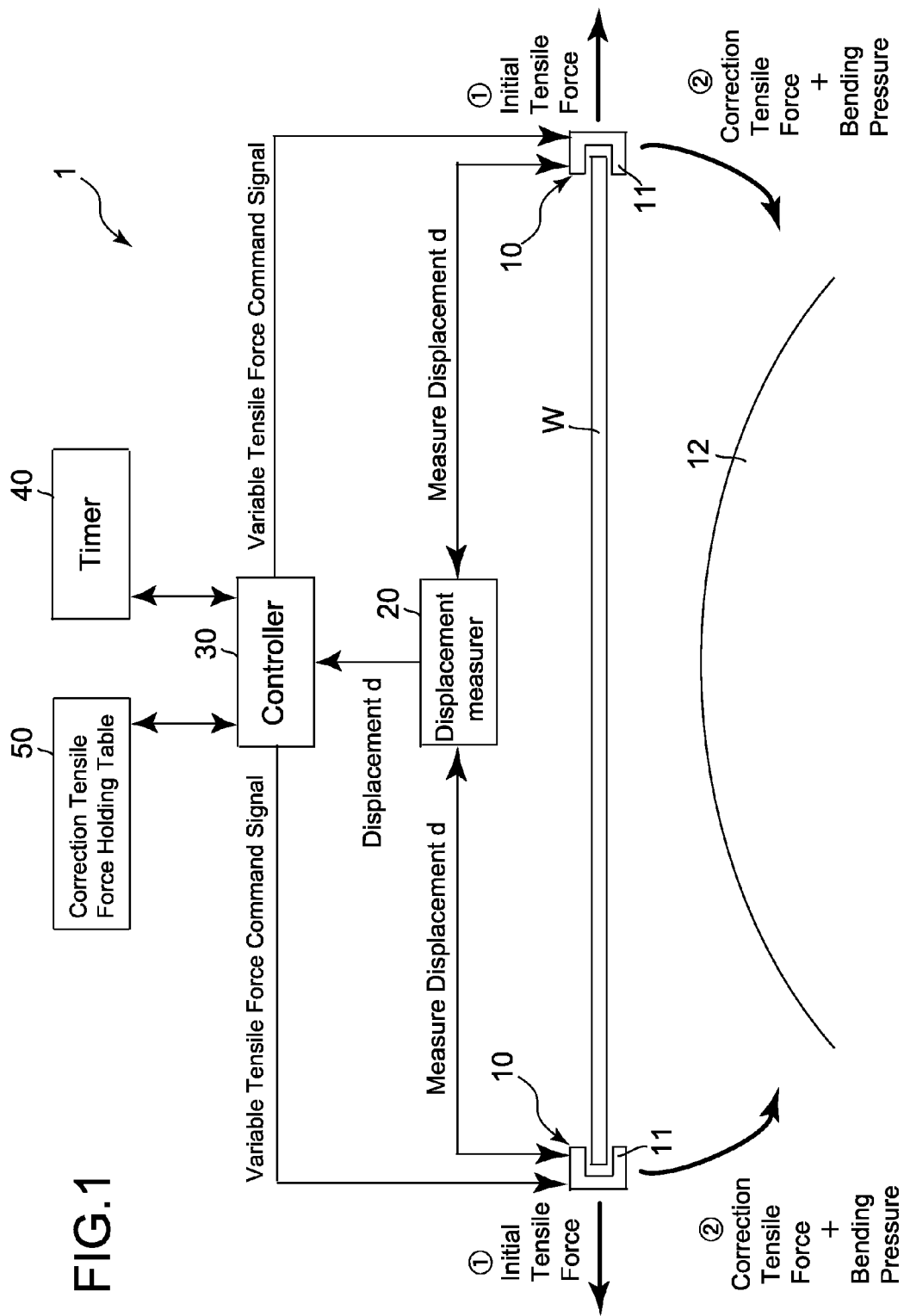
FIG. 1 is a diagram showing the configuration of a long-member bending apparatus, according to the present invention.

An embodiment in which a long-member (door-frame) bending apparatus 1 according to the present invention has been applied to a vehicle door frame production will be hereinafter discussed with reference to FIGS. 1 through 5. The long-member bending apparatus 1 is provided with benders (bending devices) 10 which applies, to a long member (door frame) W made of aluminum or iron, a variable tensile force for drawing out the long member W in the lengthwise direction, and a bending pressure for bending the long member W into a curved shape in the lengthwise direction. The benders 10 are respectively provided with chucks 11 which hold both ends of the long member W to fix the long member W, a cylinder not shown in the drawings is fixed to the chucks 11, and a variable tensile force is applied to the long member W in the lengthwise direction by applying a tensile force to the chucks 11 via the aforementioned cylinder. In addition, the chucks 11 are supported by a swingable support not shown in the drawings, and a bending pressure for bending the long member W into a curved shape in the lengthwise direction thereof is applied to the long member W by pressing the long member W against a metallic mold 12 while swinging the swingable support.

The bending apparatus 1 is provided with a displacement measurer 20 which measures a displacement d of the long member W when a tensile force is applied to the long member W, both ends of which are held by the chucks 11. The displacement measurer 20 can be, e.g., an encoder (not shown) which measures the displacement d of the long member W by converting the displacement d into a pulse number, or a system which measures the displacement d of the long member W by converting the amount of pressing a press member (not shown) pressed by the chucks 11, to which a tensile force is given into the displacement d of the long member W. Namely, the displacement measurer 20 can be of any type as long as it can measure the displacement d of the long member W.

The bending apparatus 1 is provided with a controller 30 which inputs the displacement d of the long member W, which is measured by the displacement measurer 20, to control via the benders 10 the variable tensile force applied to the long member W.

More specifically, the controller 30 sends a signal to the benders 10 commanding the benders 10 to apply a variable tensile force, to the long member W, which slowly increases from an initial tensile force; subsequently, the controller 30 commences to count time via a timer 40. Upon the displacement d of the long member W that is input from the displacement measurer 20 exceeding a tensile fracture threshold value D within a predetermined period of time, the controller 30 sends a signal to the benders 10 commanding the benders 10 to change the variable tensile force applied to the long member W to a correction tensile force which is smaller than the tensile force at the time the displacement d exceeds the tensile fracture threshold value D. Upon the predetermined period of time elapsing without the displacement d of the long member W that is input from the displacement measurer 20 exceeding the tensile fracture threshold value D, the controller 30 sends a signal to the benders 10 commanding the benders 10 to change the variable tensile force applied to the long member W to a correction tensile force which is smaller than the tensile force at the lapse of the predetermined period of time.

"Tensile fracture" herein refers to a phenomenon in which a defect such as cross-sectional distortion, deformation or rupture that is caused by an excessive elastic fracture or permanent deformation occurs in the long member W when the long member W is drawn out in the lengthwise direction for a long period of time, and in which the long member W no longer can acceptably pass as a commodity product. In addition, "tensile fracture threshold value D" refers to a displacement which may cause tensile fracture if the long member W is further drawn out when it is drawn out in the lengthwise direction by an application of a tensile force to the long member W (or a displacement slightly smaller than such a displacement). Namely, no tensile fracture has yet occurred at the moment the displacement of the long member W exceeds the tensile fracture threshold value D, so that tensile fracture can be reliably prevented from occurring if, immediately after the displacement of the long member W exceeds the tensile fracture threshold value D, the tensile force applied to the long member W is changed to a correction tensile force which is smaller than the tensile force at that time.

The controller 30 is connected to a correction tensile force holding table 50, in which a plurality of correction tensile force values for providing instructions to the benders 10 are stored to be capable of being selectively set. FIG. 2 shows an example of data stored in the correction tensile force holding table 50. The data shown in FIG. 2A shows the correlation between the time taken until the displacement d of the long member W exceeds the tensile fracture threshold value D when the displacement d of the long member W that is input from the displacement measurer 20 exceeds the tensile fracture threshold value D within a predetermined period of time and a plurality of correction tensile force values. The data shown in FIG. 2B shows the correlation between the displacement d of the long member W at a lapse of the predetermined period of time when the predetermined period of time elapses without the displacement d of the long member W that is input from the displacement measurer 20 exceeding the tensile fracture threshold value D and a plurality of correction tensile force values. In this connection, the correction tensile force holding table 50 can be stored in an internal memory of the bending apparatus 1 or an external memory which is connected to the controller 30.

Operations of the bending apparatus 1 that has been structured as above will be hereinafter discussed in detail with reference to the flow chart shown in FIG. 3. First, with both ends of the long member W held and fixed by the chucks 11 of the benders 10, the controller 30 sends a signal to the benders 10 commanding the benders 10 to apply a variable tensile force to the long member W which slowly increases from an initial tensile force, and subsequently, the controller 30 commences to count time via the timer 40. The benders 10 which have received the command signal from the controller 30 commence to apply a variable tensile force for drawing out the long member W in the lengthwise direction to the long member W by applying a tensile force to the chucks 11 via the cylinder not shown in the drawings (S1). Simultaneously, the displacement measurer 20 commences to measure the displacement d of the long member W at this application of the variable tensile force and inputs the result of this measurement to the controller 30.

Upon determining that the displacement d of the long member W that is input from the displacement measurer 20 has exceeded the tensile fracture threshold value D within a predetermined period of time (S2: YES), the controller 30 checks the time taken until the displacement d exceeds the tensile fracture threshold value D (S3), and the controller 30 refers to the correction tensile force holding table 50 and sets a correction tensile force value corresponding to the time until the displacement d exceeds the tensile fracture threshold value D (S4). For instance, in FIG. 2A, if the time taken until the displacement d exceeds the tensile fracture threshold value D is within time T1, T2 or T3, the controller 30 sets the value of the correction tensile force to A, B or C, respectively. Subsequently, the controller 30 sends a signal to the benders 10 commanding the benders 10 to change the variable tensile force applied to the long member W to the set correction tensile force. Lastly, a bending operation is performed to bend the long member W into a curved shape in the lengthwise direction by pressing the long member W against the metallic mold 12 while swinging the swingable support not shown in the drawings that supports each chuck 11 (S5).

On the other hand, upon detecting that the predetermined period of time has elapsed without the displacement d of the long member W that is input from the displacement measurer 20 exceeding the tensile fracture threshold value D (S2: No, S6: Yes), the controller 30 checks the displacement d at the lapse of the predetermined period of time (S7), refers to the correction tensile force holding table 50, and sets a correction tensile force value corresponding to the displacement d of the long member W at the lapse of the predetermined period of time (S8). For instance, in FIG. 2B, if the displacement d of the long member W at the lapse of the predetermined period of time is within displacement d1, d2 or d3, the controller 30 sets the value of the correction tensile force to X, Y or Z, respectively. Subsequently, the controller 30 sends a signal to the benders 10 commanding the benders 10 to change the variable tensile force applied to the long member W to the set correction tensile force. Lastly, a bending operation is performed to bend the long member W into a curved shape in the lengthwise direction by pressing the long member W against the metallic mold 12 while swinging the swingable support, not shown in the drawings, that supports each chuck 11 (S9).

Assuming that the tensile strength of the long member W is associated with the hardness of the material thereof, the displacement d of the long member W becomes smaller as the material of the long member W becomes greater in hardness, while the displacement d of the long member W becomes greater as the material of the long member W becomes smaller in hardness. Accordingly, if a tensile force continues to be applied in a single uniform manner to all long members W, which vary widely in tensile strength, for a predetermined period of time, the displacement d at the lapse of the predetermined period of time exceeds the tensile fracture threshold value D in some long members W (range I), while in other long members W (range II), the displacement d at the lapse of the predetermined period of time does not exceed the tensile fracture threshold value D. Although the long members W in range II cause no problems with tensile fracturing, there is a high possibility of the long members W in range I having already caused a tensile fracture at the lapse of the predetermined period of time.

Figure 3:
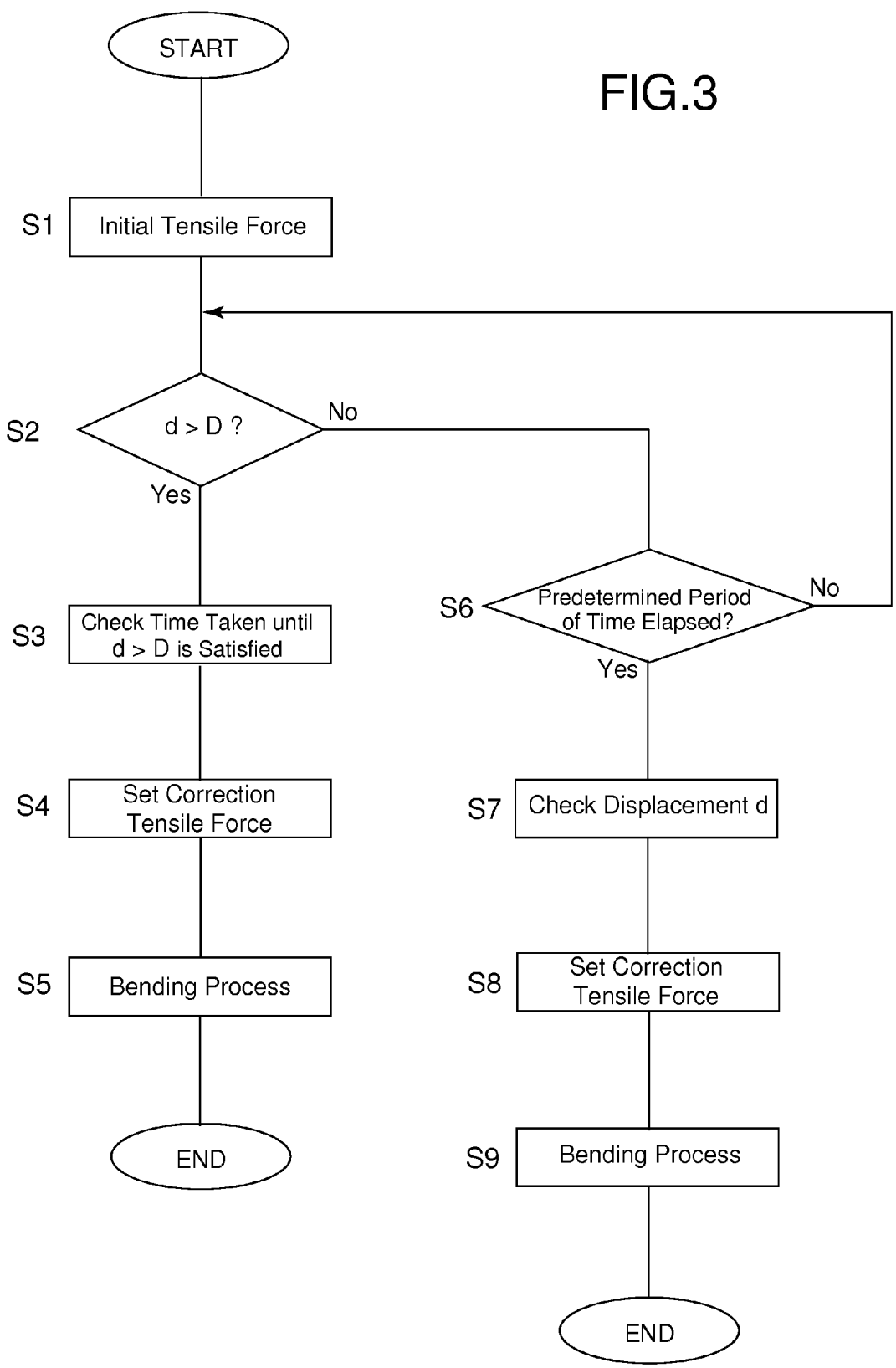
FIG. 3 is a flow chart showing a long-member bending process according to the present invention.
Figure 4:
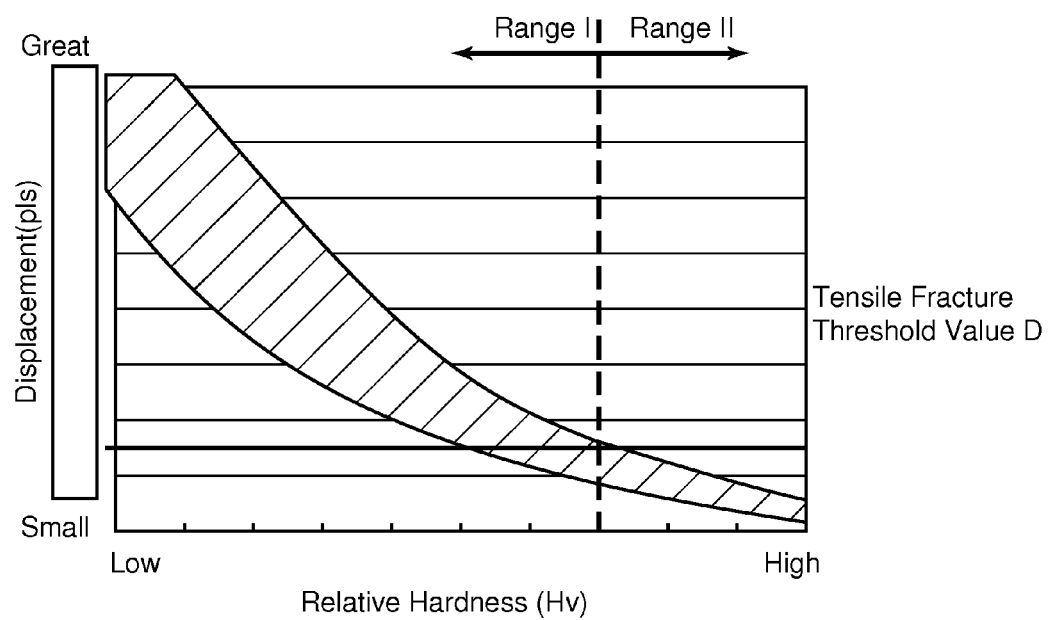
FIG. 4 is a diagram showing the difference in displacement between long members which are mutually different in hardness (tensile strength)
Figure 5:
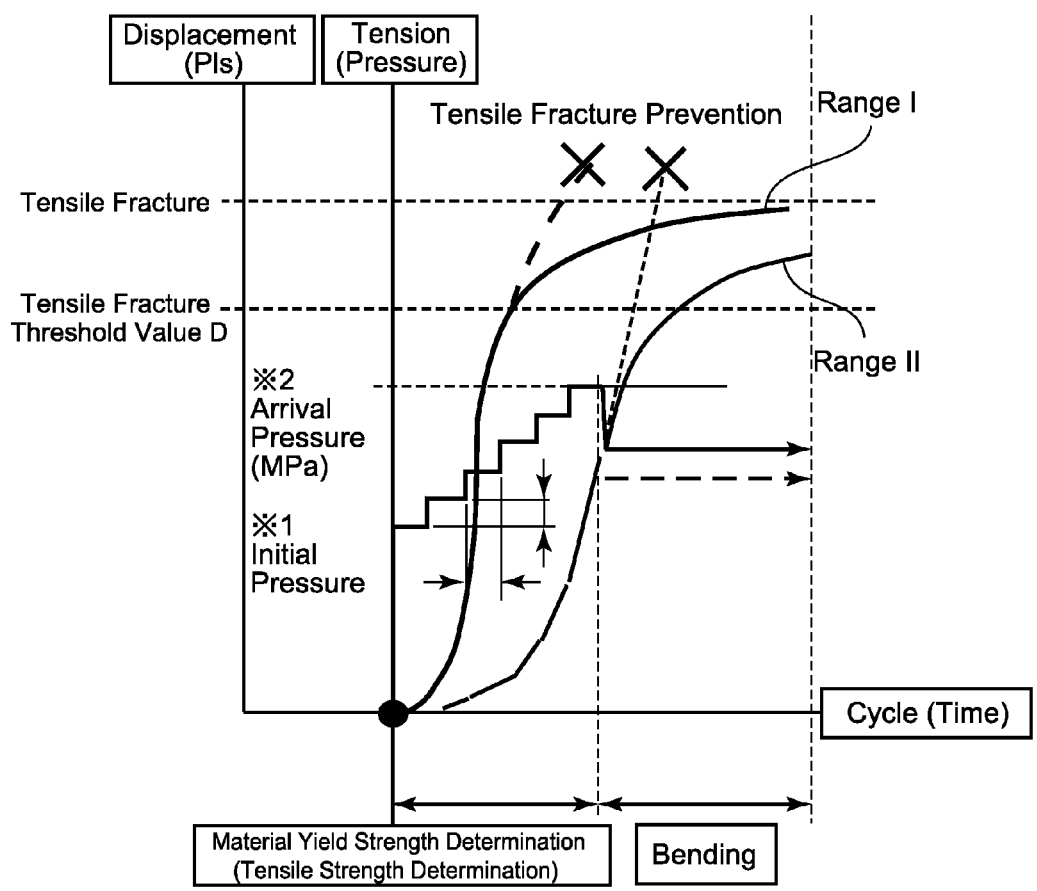
FIG. 5 is a diagram showing the control of tensile force applied to long members which vary widely in tensile strength.
Figure 6:
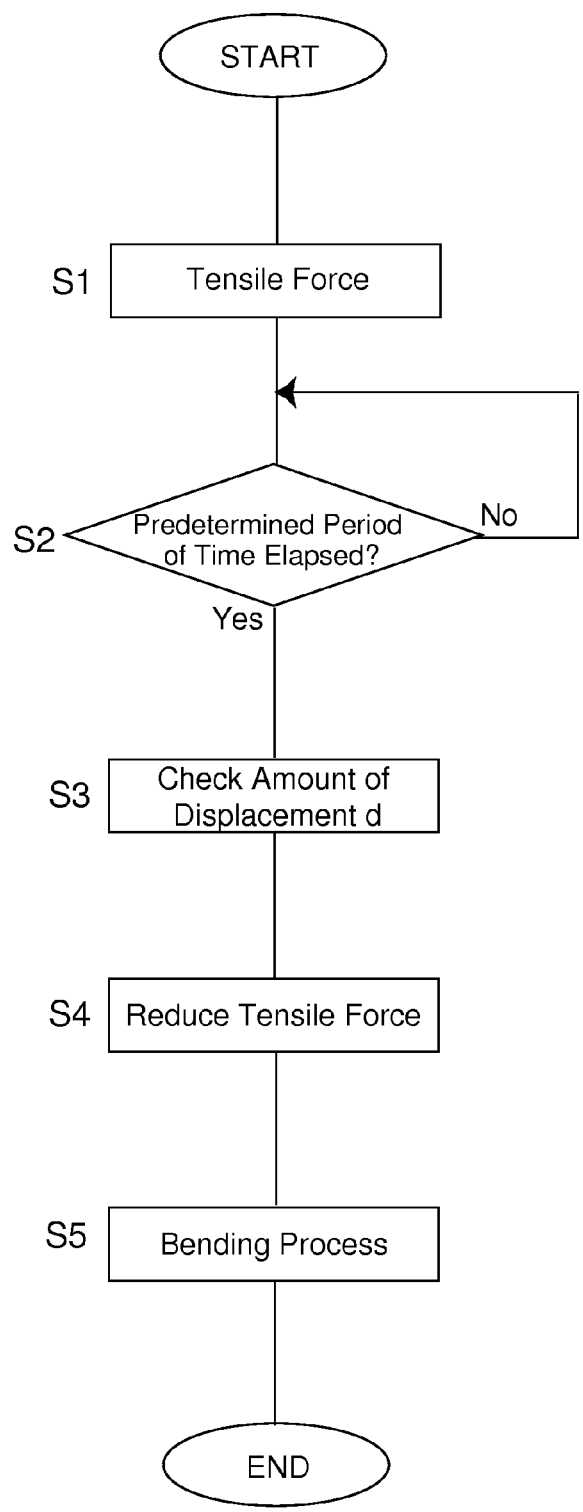
FIG. 6 is a flow chart showing a conventional long-member bending process.
Figure 7:
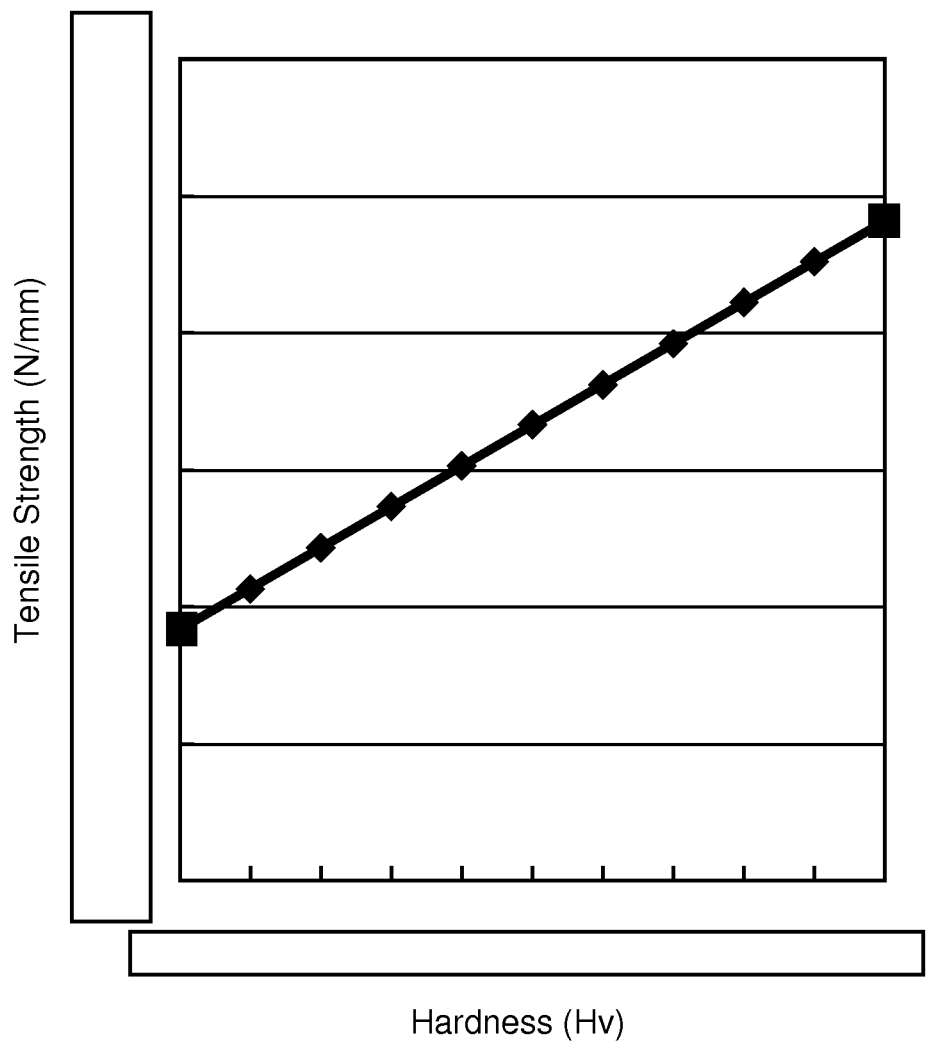
FIG. 7 is a diagram showing the general relationship between tensile strength and material hardness.

Accordingly, for the long member W in range I, immediately after the displacement d exceeds the tensile fracture threshold value D, the tensile force applied to the long member W is changed to a correction tensile force which is smaller than the tensile force at the time the displacement d exceeds the tensile fracture threshold value D to prevent a tensile fracture from occurring in the long member W as shown by a solid line in FIG. 5 (S2 through S5 in the flow chart shown in FIG. 3). In addition, for the long member W in range II, the displacement d does not exceed the tensile fracture threshold value D even after the lapse of the predetermined period of time, and after this lapse of the predetermined period of time, the tensile force applied to the long member W is changed to a correction tensile force which is smaller than the tensile force at that time, and accordingly, no tensile fracture occurs in the long member W (S2, S6 through S9 in the flow chart shown in FIG. 3).

As described above, according to the present embodiment of the long-member bending method, this method includes: a step of applying a tensile force which increases from an initial tensile force to the long member W to draw out the long member W in the lengthwise direction; a step of measuring the displacement d of the long member W after the commencement of the application of the initial tensile force; and a step of bending the long member W by applying a correction tensile force and a bending pressure for bending the long member W into a curved shape in the lengthwise direction to the long member W simultaneously, upon the displacement d exceeding the predetermined tensile fracture threshold value D within a predetermined period of time or after a lapse of the predetermined period of time without the displacement d exceeding the tensile fracture threshold value D, wherein the aforementioned correction tensile force is smaller than the tensile force at the time the displacement d exceeds the tensile fracture threshold value D or the tensile force at the lapse of the predetermined period of time; accordingly, a favorable bending process can be performed on long members W which vary widely in tensile strength, especially long members W which are low in tensile strength.

Industrial Applicability

A long-member bending method and apparatus, and a door frame bending method according to the present invention are suitable for use as a method and apparatus for bending a long member made of aluminum, iron or the like to produce, e.g., a vehicle door frame and a method of bending a door frame.

DESCRIPTION OF THE REFERENCE NUMERALS

1 Long-member bending apparatus
10 Bender (bending device)
11 Chuck
12 Metallic mold
20 Displacement measurer
30 Controller
40 Timer
50 Correction tensile force holding table
W Long member (door frame)
d Displacement
D Tensile fracture threshold value

The invention claimed is:

1. A method of bending a long member, comprising:
applying a tensile force, which increases from an initial tensile force, to said long member to draw out said long member in a lengthwise direction thereof;
measuring a displacement of said long member after commencement of said application of said initial tensile force;
bending said long member by applying a correction tensile force and a bending pressure for bending said long member into a curved shape in said lengthwise direction simultaneously to said long member upon said displacement exceeding a predetermined tensile fracture threshold value within a predetermined period of time; and
after a lapse of said predetermined period of time without said displacement exceeding said tensile fracture threshold value, said correction tensile force becomes smaller than said tensile force when said displacement exceeds said tensile fracture threshold value or said tensile force at said lapse of said predetermined period of time.

2. The long-member bending method according to claim 1, wherein, during said bending, upon said displacement of said long member after the commencement of the application of said initial tensile force exceeding said predetermined tensile fracture threshold value within said predetermined period of time, a plurality of correction tensile force values are selectively set in accordance with a time taken until said displacement exceeds said tensile fracture threshold value.

3. The long-member bending method according to claim 1, wherein, during said bending, upon said predetermined period of time elapsing without said displacement of said long member, after said commencement of said application of said initial tensile force, exceeding said tensile fracture threshold value, a plurality of correction tensile force values are selectively set in accordance with the amount of displacement of said long member at said lapse of said predetermined period of time.

4. The long-member bending method according to claim 1, wherein said long member comprises a door frame.

5. A method of bending a long member, comprising:
applying a tensile force, which increases from an initial tensile force, to said long member to draw out said long member in a lengthwise direction thereof;
measuring a displacement of said long member after commencement of said application of said initial tensile force; and
bending said long member by simultaneously applying a correction tensile force and a bending pressure to bend said long member into a curved shape;
wherein said bending comprises:
bending when said displacement of said long member exceeds a predetermined tensile fracture threshold value within a predetermined period of time, said long member is bent into said curved shape by simultaneously applying said bending pressure and said correction tensile force, which is smaller than a tensile force at the time said displacement exceeds said tensile fracture threshold value; and
bending when said predetermined period of time lapses while said displacement of said long member does not exceed said predetermined tensile fracture threshold value, said long member is bent into said curved shape by simultaneously applying said bending pressure and said correction tensile force, which is smaller than said tensile force at said lapse of said predetermined period of time.

6. An apparatus for bending a long member, comprising:

a bender which applies a variable tensile force for drawing out said long member in a lengthwise direction thereof and a bending pressure for bending said long member into a curved shape in said lengthwise direction to said long member;

a displacement measurer which measures, when said variable tensile force which increases from an initial tensile force is applied to said long member by said bender, a displacement of said long member caused by said variable tensile force; and a controller which commands, when said displacement of said long member that is measured by said displacement measurer exceeds a tensile fracture threshold value within a predetermined period of time or said predetermined period of time elapses without said displacement of said long member that is measured by said displacement measurer exceeding said tensile fracture threshold value, said bender to apply said bending pressure to said long member after changing said variable tensile force of said bender to a correction tensile force which is smaller than the variable tensile force at the time said displacement exceeds said tensile fracture threshold value or a correction tensile force which is smaller than the variable tensile force at said lapse of said predetermined period of time.

* * * * *